United States Patent [19]

Shimizu et al.

[11] 3,981,999

[45] Sept. 21, 1976

[54] FISH DISEASE TREATMENT

[75] Inventors: Masanao Shimizu, Toyonaka; Yoshiyuki Takase, Amagasaki; Kaoru Kouno, Nishinomiya, all of Japan

[73] Assignee: Dainippon Pharmaceutical Co., Ltd., Osaka, Japan

[22] Filed: Oct. 10, 1974

[21] Appl. No.: 513,824

[30] Foreign Application Priority Data
Oct. 13, 1973 Japan.............................. 48-115006

[52] U.S. Cl. ................................................. 424/251
[51] Int. Cl.² ........................................ A61K 31/505
[58] Field of Search ..................................... 424/251

[56] References Cited
OTHER PUBLICATIONS

The Merck Veterinary Manual–3rd edit. (1967) pp. 1253 and 1254.
Minami et al.–Chem. Abst. vol. 75 (1971) p. 129748c.

*Primary Examiner*—Sam Rosen
*Attorney, Agent, or Firm*—Sherman & Shalloway

[57] ABSTRACT

Pyrimidine compositions or their non-toxic acid-addition salts are used for preventing and treating infectious diseases of fish caused by pathogenic microorganisms.

13 Claims, No Drawings

FISH DISEASE TREATMENT

This invention relates to a prophylactic and therapeutic treating agent against fish diseases and to a method for preventing and treating infections diseases of fish. More specifically, it relates to the use of specific heterocyclic carboxylic acids as a prophylactic and therapeutic treating agent against bacteria-caused infectious diseases in fish.

Some chemotherapeutic agents have hitherto been used for the treatment of infectious diseases of fish on account of their corroborated effect against diseases of terrestrial mammals. Examples of such chemotherapeutic agents are furazolidone, chloramphenicol, tetracycline and sulfisoxazole. Microorganisms which cause diseases in fish are, however, not exactly the same as those which effect terrestrial mammals, and the ecological and physiological behaviours of fish are much different from those of terrestrial mammals. Therefore, the unerring effectiveness of the chemotherapeutic agents on various pathogenic microorganisms in fish is dubious, and may not be assumed.

However, even when these drugs are used, achievement of the prevention or treatment of these fish diseases is difficult in many cases because of the development of drugresistant bacteria and of the limited method of using these drugs.

We have now found that a heterocyclic carboxylic acid of the formula

R—COOH           (I)

wherein
R represents a heterocyclic radical selected from the group consisting of 5,8-dihydro-2-pyrrolidino-8-ethyl-5-oxopyrido[2,3-d]pyrimidin-6-yl, 1,4-dihydro-7-(4-methyl-1-piperazinyl)-4-oxo-1-vinyl-quinolin-3-yl, 1,4-dihydro-7-(4-ethyl-1-piperazinyl)-4-oxo-1-vinylquinolin-3-yl and 1,4-dihydro-7-(1-piperazinyl)-4-oxo-1-vinyl-1,8-naphthyridin-3-yl, or its non-toxic acid addition salt has an excellent effect against microorganisms which cause fish diseases (for example, Chondrococcus columnaris or Vibrio anguillarum) with reduced toxicity on fish, and can therefore be used favorably as a prophylactic and therapeutic agent for infectious diseases of fish.

Accordingly, a basc object of this invention is to provide a method for using the compound of formula (I) described above as a prophylactic and therapeutic agent against fish diseases.

Another object of this invention is to provide a prophylactic and therapeutic agent which exerts an unerring and marked effect against microbial infections in fish with no material toxicity.

Another object of the invention is to provide a composition for prophylaxis and therapy of infectious diseases of fish.

A further object of the invention is to provide a method for preventing and treating infectious diseases of fish.

These and other objects of the invention will become more apparent from the following description.

The present invention thus provides a preventing and treating agent against bacteria-caused diseases of fish comprising as an active ingredient at least one heterocyclic carboxylic acid of the above formula (I) or its acid addition salt; a method for controlling bacteria-caused infectious diseases in fish which comprises applying at least on heterocyclic carboxylic acid of formula (I) given above or its nontoxic acid addition salt to said fish in an amount effective to prevent or control said infectious diseases; and also a composition or bathing-solution containing said heterocyclic carboxlic acid or its non-toxic acid addition salt.

The heterocyclic carboxylic acid of formula (I) described above is specifically illustrated as follows:
1. 5,8-Dihydro-2-pyrrolidino-8-ethyl-5-oxopyrido[2,3-d]pyrimidine-6-carboxlic acid

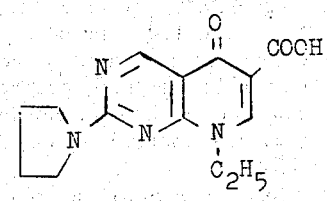

(PA for short)

2. 1,4-Dihydro-7-(4-methyl-1-piperazinyl)-4-oxo-1-vinylquinoline-3-carboxylic acid

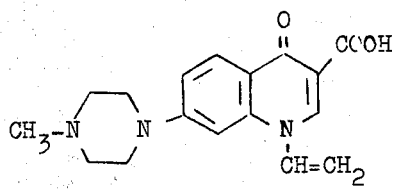

(AT-1493 for short)

3. 1,4-Dihydro-7-(4-ethyl-1-piperazinyl)-4-oxo-1-vinylquinoline-3-carboxylic acid

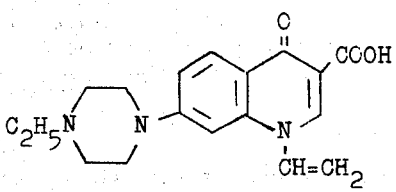

(AT-1557 for short)

4. 1,4-Dihydro-7-(1-piperazinyl)-4-oxo-1-vinyl-1,8-naphthyridine-3-carboxylic acid

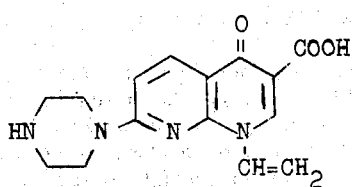

(AT-1475 for short)

Of these, 5,8-dihydro-2-pyrrolidino-8-ethyl-5-oxopyrido[2,3-d]pyrimidine-6-carboxylic acid [PA] is especially preferred as a prophylactic and therapeutic treating agent against fish diseases.

The above heterocyclic carboxylic acid of formula (I) can be used also in the form of a non-toxic acid addition salt. Inorganic acids such as hydrochloric acid and organic acids such as acetic acid or methanesulfonic acid are suitable as the acid that can be used to form these acid addition salts.

All of the above compounds of formula (I) are known as antibacterial agents for human and mammals (see British patent specification No. 1,129,359 and German Offenlegungsschrift Nr. 2362553).

The term "fish", used in the present application, has a very wide sense covering a variety of fish which may be kept, raised or cultured as foods, pets or other useful materials in connection with the human life, and especially includes fish in an ordinary sense and also crustaceans and shellfish.

The fish to which the agent of the present invention can be applied include that living in fresh water, brackish water and salt water. Specific examples of such fish are yellow tail, saurel, trout, flat-fish, sillago, sea bream, codfish, horse mackerel, bonito, tunny, gray mullet, salmon, rainbow trout, shrimp, prawn, sea eel, eel, mud fish, carp, silver carp, dace, ayu, angel fish, guppy, platy fish, gold fish, ear-shell, top-shell, oyster and pearl oyster.

It is well known that in raising or cultivating fish of the type described, various infectious diseases often develop and spread, and may result in the death of the fish. These infectious diseases caused by bacteria occur frequently for whole seasons, and fish culturists are very much concerned with these diseases. The causes of these diseases are various bacteria such as Genus Aeromonas, Chondrococcus columnaris, and Genus Vibrio.

The antimicrobial activity of the heterocyclic carboxylic acid of formula (I) of the present invention is seen on various bacteria pathogenic to fish, of which examples are Vibrio, Aeromonas, Chondrococcus, Pasteurella, and Pseudomonas anguilliseptica.

The excellent controlling effects of the compounds of the formula (I) on infectious diseases of fish will become apparent from the following tests.

1. Effect on various pathogenic microorganisms to fish in vitro.

Test method:

The MIC (minimum inhibitory concentration) of a test compound was determined by the serial dilution method on various pathogenic microorganisms incubated under the following experimental conditions. The lowest concentration at which the visible growth of the organism was inhibited was considered as MIC.

Experimental conditions:
Method:
   the broth-dilution method
Medium:
   bouillon, pH 7.2, except for Vibrio (3% NaCl-bouillon, pH 7.2), Pasteurella (2% NaCl-Brain Heart Infusion, pH 7.3 and Chondrococcus (TY medium, pH 7.3)
Inoculum:
   1 drop of a bacterial suspension per test tube (100 - 1000 minimal growing units in the medium)
Incubation temperature:
   25°C, except for Pseud. anguilliseptica (20°C)
Incubation time:
   48 hours, except for Pseudo. anguilliseptica (7 hours)

Table 1

| Organisms | MIC : μg/ml | | | | Tetra-cycline |
|---|---|---|---|---|---|
| | PA | AT-1493 | AT-1557 | AT-1475 | |
| Aeromonas liquefaciens Y-62 | 1 | 0.1 | 0.3 | 0.3 | 1 |
| Aeromonas salmonicida Hara-1 | 0.1 | 0.1 | 0.3 | 0.3 | 0.3 |
| Aeromonas salmonicida Hara-2 | 1 | 0.1 | 0.3 | 1 | 0.1 |
| Aeromonas salmonicida Kawazu | 0.1 | 0.1 | 0.1 | 0.3 | 1 |
| Aeromonas salmonicida Kusuda | 0.1 | 0.1 | 0.3 | 0.3 | 0.3 |
| Vibrio anguillarum A-8 | 3 | 3 | 3 | 10 | 1 |
| Vibrio anguillarum K-3 | 1 | 3 | 10 | 3 | 1 |
| Vibrio anguillarum Km-30 | 3 | 3 | 10 | 10 | 0.3 |
| Pasteurella piscicida Al-3 | 0.3 | 1 | 1 | 1 | 0.3 |
| Pasteurella piscicida K-1 | 1 | 0.3 | 1 | 1 | 0.3 |
| Pseudomonas anguilliseptica S-1 | 0.1 | 0.1 | 0.1 | 0.1 | 0.3 |
| Pseudomonas anguilliseptica T-2 | 0.1 | 0.1 | 0.1 | 0.1 | 0.3 |
| Chondrococcus sp K-1 | 0.3 | 3 | 1 | 1 | 1 |
| Chondrococcus sp K-2 | 0.3 | 3 | 1 | 1 | 1 |

It will be seen from the above results that all of the compounds of formula (I) in accordance with the present invention possess excellent antimicrobial effects in vitro against microorganisms causing fish diseases to the same extent as tetracycline which is a known antibacterial agent.

2. Oral effect against Aeromonas infection in goldfish

Test method:

Goldfish each weighing about 6 – 7 g were given a fish food containing each of the test compounds. After 30 minutes, the fish were infected intramuscularly with Aeromonas liquefacieus Y-62 (about $10^7$ germs/fish) under ether anesthesia. The fish were observed for the following 5 days after infection, while keeping the water temperature at 24° – 25°C. In the same manner, the control group was given the same fish food without the test compound.

Table 2

| Drug | Conc. in diet (%) | Dose (mg/kg) | Number of surviving fish after the period indicated (days) | | | | | | Percent survival |
|---|---|---|---|---|---|---|---|---|---|
| | | | 0 | 1 | 2 | 3 | 4 | 5 | |
| PA | 0.1 | 6.1 | 10 | 10 | 10 | 10 | 10 | 10 | 100 |
| | 0.03 | 2.5 | 10 | 10 | 9 | 7 | 6 | 6 | 60 |
| AT-1493 | 0.1 | 7.5 | 5 | 5 | 5 | 5 | 5 | 5 | 100 |
| | 0.03 | 2.5 | 5 | 5 | 5 | 5 | 5 | 5 | 100 |
| AT-1557 | 0.1 | 7.6 | 5 | 5 | 5 | 5 | 5 | 5 | 100 |
| | 0.03 | 2.2 | 5 | 5 | 4 | 4 | 4 | 4 | 80 |
| AT-1475 | 0.3 | 22.3 | 5 | 5 | 5 | 5 | 5 | 5 | 100 |
| | 0.1 | 7.5 | 5 | 5 | 4 | 4 | 3 | 3 | 60 |
| Tetracycline | 3 | 253.1 | 5 | 5 | 1 | 0 | — | — | 0 |
| | 1 | 80.4 | 5 | 3 | 0 | 0 | — | — | 0 |
| Control | — | — | 10 | 3 | 1 | 0 | — | — | 0 |

The compounds of formula (I) all showed a percent survival of at least 60% in a diet concentration of 0.03 to 0.1% (about 2.2 to 7.6 mg/kg). In contrast, tetracycline and compound E showed a percent survival of zero percent in a diet concentration of as high as more than 0.1% as well as in a concentration of as low as 0.1%. Accordingly, it is clear that the compounds of formula (I) of the present invention show far better effects in a small oral dose than the known antimicrobial agents.

3. Bathing effect against Aeromonas infection in goldfish

Test method:
Goldfish each weighing about 8 g were infected intramuscularly with Aeromonas liquefaciens Y-62 ($10^7$ germs/fish) under ether anesthesia. The fish were grouped and each group was placed in 6 liters of fresh water (23° to 27°C.) containing PA in the amount indicated in Table 3.

Then, observation was made for the following 5 days. In the same manner, the control group was placed in 6 liters of fresh water without any test compound incorporated in it.

Table 3

| Drug | Bathing conc. (μg/ml) | Number of survival after the period indicated (day) | | | | | | Percent survival |
|---|---|---|---|---|---|---|---|---|
| | | 0 | 1 | 2 | 3 | 4 | 5 | |
| PA | 1 | 6 | 6 | 6 | 6 | 6 | 6 | 100 |
| | 0.5 | 6 | 6 | 6 | 6 | 6 | 6 | 100 |
| Untreated control | — | 6 | 1 | 0 | — | — | — | 0 |

4. Toxicity
Oral toxicity in goldfish:
A diet containing 10% of each of the test compounds was given orally to groups each consisting of 5 goldfish each weighing 6 to 10 g, and observation was made for the following 7 days. The temperature of the water was maintained at 28°C. The results are shown in Table 4.

Table 4

| Drug | Dose (mg/kg) | Number of the survival after indicated period (days) from administration | | | | | | | | Mortality (%) |
|---|---|---|---|---|---|---|---|---|---|---|
| | | 0 | 1 | 2 | 3 | 4 | 5 | 6 | 7 | |
| PA | 800 | 5 | 5 | 5 | 5 | 5 | 5 | 5 | 5 | 0 |
| AT-1493 | 955 | 5 | 5 | 5 | 5 | 5 | 5 | 5 | 5 | 0 |
| AT-1557 | 935 | 5 | 5 | 5 | 5 | 5 | 5 | 5 | 5 | 0 |
| AT-1475 | 923 | 5 | 5 | 5 | 5 | 5 | 5 | 5 | 5 | 0 |
| Untreated control | — | 5 | 5 | 5 | 5 | 5 | 5 | 5 | 5 | 0 |

Oral toxicity in eels:
A suspension of PA in 0.2% carboxymethylcellulose was orally given to groups each consisting of 10 eels (Anguilla Japonica, about 160 g) and observation was made for the following 7 days. The temperature of the water was kept at 27° to 27.5°C.

All eels survived without abnormality of their external appearance at a dose of 2000 mg/kg.

Bathing toxicity in goldfish:
Groups of goldfish each weighing 7 to 8 g (each group consisting of 6 goldfish) were placed in 6 liters of fresh water (27° to 30°C.) containing PA in varying concentrations with aeration for 5 days. During this time, observation was made. As shown in Table 5, the $LC_{50}$ (50% lethal concentration) value of PA for the goldfish was 10.13 μg/ml.

Table 5

| Drug | Bathing conc. (μg/ml) | Number of the survival after the period indicated (day) | | | | | | Mortality (%) | $LC_{50}$ μg/ml |
|---|---|---|---|---|---|---|---|---|---|
| | | 0 | 1 | 2 | 3 | 4 | 5 | | |
| PA | 16 | 6 | 6 | 6 | 1 | 0 | — | 100 | |
| | 8 | 6 | 6 | 6 | 5 | 5 | 5 | 20 | 10.13 |
| | 4 | 6 | 6 | 6 | 6 | 6 | 6 | 0 | |
| Untreated control | — | 6 | 6 | 6 | 6 | 6 | 6 | 0 | |

According to the present invention, the compound of formula (I) can be applied to fish in whom microbial infections are desired to be prevented or cured. This can be done in various modes. One of the typical modes is to administer the compound of formula (I) as such or a composition containing the compound of formula (I) orally to fish. Another typical mode is to give fish a food or diet having admixed therewith the compound of formula (I). Another mode is to treat fish temporarily or continuously with an aqueous solution (bath) of the compound of the formula (I) by immersing or washing. A further mode is to cultivate fish in an appropriate medium (e.g., fresh water, brackish water, or sea water containing the compound).

The compound of formula (I) can be applied as such, but generally, it is suitable to administer it orally in the form of an orally administrable composition comprising at least one heterocyclic carboxylic acid of formula (I) or its nontoxic acid addition salt and a suitable diluent. The composition may be a solid such as a powder, tablet or granule or a liquid such as a suspension or solution. The diluent used for this purpose may be, for example, water, ethanol, starch, dextrin, talc, gelatin, lactose, bentonite, fish powder, or sucrose. These diluents may be used alone or in combination of two or more.

The above composition can contain the active compound of formula (I) in an amount of from 0.1 to 99% by weight, preferably 0.5 to 50% by weight, based on the weight of the composition. The remainder may be a diluent of the type described.

The active compound of formula (I) may be incorporated in foods or diets for fish. The amount of the active compound of formula (I) to be incorporated can be varied according to the type of the fish, and the type of the food or diet, etc. But generally, it is 0.001 to 10% by weight, preferably 0.01 to 1% by weight, based on the weight of the food or diet.

The active compound of formula (I) may also be incorporated in a fish treating and immersing bath.

Thus, according to this invention, there is also provided a fish treating and immersing bath for preventing and treating infectious diseases of fish caused by bacteria comprising 0.05 to 500 ppm of at least one compound of formula (I) or its non-toxic acid addition salt in water. The concentration of the active ingredient can be 0.1 to 500 ppm, preferably 0.5 to 100 ppm, for temporary bathing, and 0.05 to 5 ppm, preferably 0.1 to 1 ppm, for bathing for a prolonged period of time (i.e., cultivation in an aqueous solution of the active ingredient).

In order to increase its solubility in water, the heterocyclic carboxylic acid of formula (I) can be used in the form of its alkali metal salt, especially its sodium salt. Alternatively, it may be incorporated in water as an admixture with a small amount of a water dispersing agent such as carboxymethylcellulose (CMC), hydroxypropylcellulose or gelatin.

The amount of the compound of formula (I) to be applied is dependent upon numerous factors such as the species, size and age of fish, the kind of infection, the circumstances surrounding the fish, or the mode of application. Therefore, it should be appropriately determined in each case. For example, the dose of the active ingredient in oral administration is normally from 0.5 to 500 mg per kilogram of body weight.

As described above, the compounds of formula (I) exert a high antimicrobial activity against various microorganisms pathogenic to fish without showing any material toxicity in fish. Their prophylactic effects are especially outstanding, and can be obtained using a very small dose. Although the compounds of the present invention show good effects when used for bathing, they especially exhibit superior effects in oral administration. Since there are a very few excellent orally administrable agents, the orally administrable compositions of this invention contribute greatly to the industry, and are very valuable.

The following Examples further illustrate the present invention.

EXAMPLE 1

Curing effect in oral administration

Using groups of goldfish each consisting of 20 goldfish (10g) naturally infected with Chondrococcus columnaris, the curing effect of PA in oral administration was examined.

PA was incorporated in a powdered fish diet, and the diet was given to fish for 3 days (2% of bodyweight/day), two times daily, once in the morning and again in the evening. The rate of survival was observed for 7 days. It was found that the rate of survival was 70 to 80% when the amount of PA in the diet was 0.1% and 0.01%.

In a control group fed with the same diet without the drug, 80% of the fish died during the experimental period.

EXAMPLE 2

Groups of eels (Anguilla Japonica, average weight 100 g) (each group consisting of 50 fish) were infected intramuscularly with Aeromonas liquefaciens Y-62 ($10^9$ germs/fish). For 2 days starting at the day before infection, a suspension consisting of a diet containing PA was orally administered to the eels using a catheter at a dose of 1.56 mg/kg/day. On the seventh day after the infection, the eels were observed. It was found that 80% of the eels survived.

In a control group (50 eels) to which the drug was not applied, all the fish died before 3 days passed after being infected.

During the experimental period, the temperature of the water was maintained at 25° to 26°C.

EXAMPLE 3

Groups of eels (Anguilla Japonica, average weight 100 g) (each group consisting of 50 eels) were infected intramuscularly with Aeromonas liquefaciens Y-62 ($10^9$ germs/fish). A suspension consisting of a diet containing PA was orally administered to the eels at 4 hours after the infection and on the next day, using a catheter, at a dose of 3.1 mg/kg/day. The eels were observed on the seventh day after the infection, and it was found that the rate of survival was 100%.

In a group (50 fish) to which the drug was not applied, all the fish died within 3 days after the infection.

The temperature of the water was kept at 25° to 26°C. during the entire experimental period.

| | Example A |
|---|---|
| PA | 300 g |
| Polyvinyl pyrrolidone | 10 g (5% solution) |
| Lactose | 40 g |
| Starch | 50 g |

The above ingredients were kneaded, size-adjusted, and dried in a customary manner to form a granular composition.

| | Example B |
|---|---|
| AT-1493 | 300 g |
| Gelatin | 6 g (10% solution) |
| Dextrin | 40 g |
| Starch | 54 g |

The above ingredients were kneaded, size-adjusted and dried in a customary manner to form a granular composition.

| Example C | |
|---|---|
| PA | 300 g |
| Lactose | 1350 g |
| Starch | 1350 g |

The above ingredients were mixed to form a 10% powder.

In the same way as in Examples A, B and C, granular compositions or powdery compositions containing AT-1475 and AT-1557 as a main ingredient respectively could be prepared.

| Example D Recipe of a goldfish diet: | |
|---|---|
| Flour + Corn powder | 850 g |
| Fish powder | 90 g |
| Mineral | 40 g |
| Vitamines | Small amount |
| Other matter | about 20 g |
| Total | 1000 g |

The above goldfish diet was admixed with 30 mg of PA, and water was added to knead the mixture thoroughly. The mixture was then formed into granules each having a diameter of about 1 mm.

What we claim is:

1. A method for controlling a bacteria-caused infectious disease in fish which comprises administering a composition of 5,8-dihydro-2-pyrrolidino-8-ethyl-5-oxopyrido[2,3-d]pyrimidine-6-carboxylic acid or its non-toxic acid-addition salt in a suitable carrier to said fish in an amount effective to prevent or control said infectious disease.

2. The method of claim 1 wherein said composition is orally administered to the fish.

3. The method of claim 1 wherein said fish is treated by immersion in water containing said composition for a short but sufficient time for said compound to make contact with the fish and then placed in water free of said composition.

4. The method of claim 1 wherein said fish is treated by contacting continuously with water containing said composition.

5. The method of claim 1 wherein said fish is fed with a food or diet containing said effective amount.

6. The method of claim 2 wherein the composition is admixed with a diluent prior to administration so that the composition is present in from 0.1 to 99 percent by weight, based upon the weight of the admixture.

7. The method of claim 2 wherein the composition is admixed with a diluent prior to administration so that the composition is present in from 0.5 to 50 percent by weight, based upon the weight of the admixture.

8. The method of claim 3 wherein the concentration of the composition is from 0.1 to 500 ppm.

9. The method of claim 3 wherein the concentration of the composition is from 0.5 to 100 ppm.

10. The method of claim 4 wherein the concentration of the composition is from 0.05 to 5 ppm.

11. The method of claim 4 wherein the concentration of the composition is from 0.1 to 1 ppm.

12. The method of claim 5 wherein the amount of the composition is from 0.001 to 10 percent by weight, based upon the weight of the food or diet.

13. The method of claim 5 wherein the amount of the composition is from 0.01 to 1 percent by weight, based upon the weight of the food or diet.

* * * * *